(12) United States Patent
Thies

(10) Patent No.: US 7,192,603 B2
(45) Date of Patent: *Mar. 20, 2007

(54) PEST CONTROLLING

(75) Inventor: Curt Thies, St. Louis, MO (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/337,513

(22) Filed: Jan. 7, 2003

(65) Prior Publication Data

US 2003/0124167 A1   Jul. 3, 2003

(51) Int. Cl.
*A01N 25/32* (2006.01)

(52) U.S. Cl. .................. 424/406; 424/405; 424/408

(58) Field of Classification Search ............... 424/405, 424/406, 408
See application file for complete search history.

(56) References Cited

U.S. PATENT DOCUMENTS

| 4,376,113 | A | * | 3/1983 | Suglia et al. | ............... | 424/494 |
| 4,615,883 | A | | 10/1986 | Nelsen et al. | | |
| 5,120,349 | A | * | 6/1992 | Stewart et al. | ............... | 504/234 |
| 5,576,008 | A | | 11/1996 | Yang et al. | | |
| 5,596,051 | A | | 1/1997 | Jahns et al. | | |
| 5,866,153 | A | | 2/1999 | Hasslin et al. | | |
| 6,001,346 | A | | 12/1999 | Delwiche et al. | | |

FOREIGN PATENT DOCUMENTS

FR        259 1857      6/1987
WO        982 4317      6/1998

OTHER PUBLICATIONS

Pepperman, Armand et al., "Controlled Release Formulations of Alachlor Based on Calcium Alginate," Journal of Controlled Release 34: 1995; pp. 17-23.
Omi, S., et al., "Microencapsulation of pheromone-analogue and measurement of the sustained release," J. Microencasulation, 1991, vol. 8, No. 4, 465-478 (1991).

* cited by examiner

*Primary Examiner*—Neil S. Levy
(74) *Attorney, Agent, or Firm*—Fish & Richardson, P.C.; Charles Hieken

(57) ABSTRACT

The present invention features a sustained-release microcapsule for long-term pest controlling. In general, a microcapsule has a capsule core including active pest-control ingredients and diluents, and a capsule shell which physically separates the capsule core from the surrounding medium. Diluents are arranged to entrap active ingredients therein and to provide resistance to mass transfer of the active ingredients therethrough. The capsule shell generally includes the shell pores and provides additional resistance to mass transfer of the active ingredient therethrough. Diluents are selected from a class of material such that the mass transfer resistances existing in the capsule core and/or capsule shell depend on the temperature of the surrounding medium.

6 Claims, No Drawings

PEST CONTROLLING

This invention relates to pest controlling and more particularly to a sustained-release, long-term pest-control microcapsule which is environmentally friendly and nontoxic.

Use of microcapsules containing various active pest-control agents is well known. Several patents disclose such microcapsules, e.g., U.S. Pat. No. 3,429,827, 3,577,515, 4,280,833, 4,285,720, 4,417,916, 4,900,551, and 4,936,901. Interfacial polycondensation is often used as the technique to form microcapsules loaded with active pest-control agents, although techniques including complex coacervation and in situ polymerization can also be used. These and other microencapsulation techniques for preparing microcapsules have been described in various review articles. *Microencapsulation*, Thies, C., Kirk-Othmer Encyclopedia of Chemical Technology, 4th ed., Vol. 16, John Wiley, N.Y., 1995, pp 628–652. *Microcapsule Processing and Technology*, Kondo, A., (edited and revised by J. Wade van Valkenburg), Marcell Dekker, N.Y., 1979. *Mikrokapseln*, Sliwka, W., Ullmmanns Encyklopadie der technischen chemie, Vol. 16, Verlag Chemie, Weinhein, 1978, pp 675–682.

It is an important object of the invention to provide improved methods and means for pest controlling.

The invention features a sustained-release, long-term pest-control microcapsule which prolongs its potency adaptive to the temperature of the surrounding medium and which is environmentally friendly and nontoxic.

One aspect of this invention relates to a pest-control microcapsule which releases an active pest-control agent at a sustained rate, thereby prolonging the potency of the microcapsule. In general, a microcapsule includes a capsule core and a capsule shell. Historically, it has not been recognized that both the shell and core can provide resistant paths to the mass transfer of active pest-control agent contained in the capsule core. The pest-control microcapsule of the present invention utilizes this new concept, thereby reducing the rate of release of active ingredient distributed to the surrounding medium, thereby extending the length of performance of the capsules in the field, and reducing the cost of pest control as well as the potential for environmental pollution. Furthermore, candidate diluents are biodegradable materials compatible with the environment.

The diluent is distributed in the core in such a manner that the active pest-control agent is effectively bound by the diluent and diffuses through the resistant paths formed by the diluent to reach the capsule shell through which it then diffuses. The diluent may form a solid-like, matrix-like or mesh-like structure inside the core and entrap the active ingredient inside such matrix and mesh. The diluent may also simply form a homogeneous solution with the active ingredient (AI) in which the AI and diluent interact (i.e., AI-diluent interaction), thereby slowing release of the AI from the capsule. Accordingly, a formulator can obtain desirable permeability or release rate of the active ingredient by manipulating several factors, such as the amount or percentage of the diluent contained in the capsule core, distribution pattern of the diluent in the core, method of entrapping the active ingredient in the diluent, and other physical properties of the diluent.

The capsule shell separates the core volume material from the surrounding medium, and is arranged to provide additional resistant paths to diffusion of the active ingredient from the capsules. Thus, permeability or release rate of the active ingredient can be manipulated by controlling several features of the shell such as pore size, length, density, tortuosity, pattern of pore distribution, and other physical properties of the material composing the shell.

A pest-control microcapsule can be composed in such a way that the permeability or release rate of the active ingredient depends upon the physical and/or chemical properties and melting point of the diluent and the temperature of the surrounding medium. Lipids such as oils, waxes, and fats with at least one ester linkage or cholesterol are used as diluents and incorporated into the capsule core through microencapsulation. In general, these lipids have melting points of 80° C.–90° C., but some lipids may form liquids at room temperature. Melting of lipid solids may occur over a wide range of temperature, especially when the diluent consists of a mixture of various lipids with different melting points or when those lipids are solids at or just below room temperature (e.g., 20°–30° C.). When the temperature of the surrounding medium rises near or above the melting point of the lipid, i.e., usually during the season and/or the time of the day with high insect activity or mating, the lipid diluent begins to soften or melt, and the active ingredient previously entrapped by the solid diluent is able to diffuse from the capsule at a higher rate. However, when the temperature falls below the melting point of the lipid and enough to suppress insect activities, the lipid diluent hardens or solidifies and effectively sustains the release of the active pest-control agent by re-entrapping the agent in the hardening or solidifying lipid.

In general, the lipid has a relatively high boiling point, e.g., higher than 200° C. at atmospheric pressure and, therefore, hardly evaporates. Accordingly, the potency of the pest-control microcapsule can be effectively prolonged adaptive to the temperature of the surrounding medium. It is appreciated that lipids capable of prolonging functionality of the capsules may melt below room temperature. In this case, the lipid-active ingredient interactions alone in the liquid state prolong release of the active ingredient from the capsules. That is, the pest-control microcapsule includes, in its core, a lipid diluent that is capable of dissolving the active pest-control agent in liquid state to form a homogeneous solution at room temperature (20°–30° C.). By mixing such diluent with the active ingredient, a formulator can effectively entrap the active ingredient within the lipid diluent. When using lipid diluents that are solids at the room temperature, the formulator can customize the melting point of the diluent by manipulating the molecular size and chemical structure of the lipid. For example, the melting point of the lipid including oils, waxes, and fats can vary over a wide range of temperature by manipulating the number of ester linkages as well as the number and characteristics of the short-, medium-, and long-chained fatty acids attached to those ester linkages.

Lipids with aforementioned properties can be obtained from a variety of sources, including minerals, plants, and animals, and may be manufactured by chemical synthesis. Such lipids may be used in their natural form or may be treated by mechanical or chemical processes including filtration, purification, distillation, hydrogenation, and selective crystallization. Examples of those lipids include mineral oil, plant oil, animal oil, animal fat, butterfat oil, butter fat, lard, natural wax, beeswax, insect wax, candellila wax, carnauba, hydrogenated tallow or various plant oils, paraffin wax, and the like. Yet other examples of such lipids include monoglyceride, diglyceride, and triglyceride such as tristearin, tripalmitin, and trilaurin, with or without a free fatty acid.

The sustained-release, pest-control microcapsule of the present invention can be composed of biodegradable and nontoxic compounds. The pest-control microcapsule can include in its core a biopesticide (such as pheromones, pyrethroids, insect growth regulators, and insect attractants or repellents) and an inactive, biodegradable and non-toxic lipid diluent (such as oils, waxes, and fats with ester linkages or cholesterol). However, conventional toxic pest-control agents can also be used along with the inactive, biodegradable, and nontoxic lipid diluent.

The pest-control microcapsule of the present invention can have a density lighter than or comparable to that of water. Generally, lipid diluents are lighter than water and, therefore, microcapsules containing sufficient amount of such lipids float in an aqueous solution on storage. The creamed layer formed by clogged microcapsules may adversely affect the potency and performance characteristics of the microcapsules, unless the capsule slurry is properly formulated. Accordingly, a water-immiscible compound, having at least one ester linkage and having a density greater than that of water, may be added to the lipid diluent in an amount effective to make the microcapsules sink slowly in an aqueous solution or suspending medium. Such water-immiscible compounds can also be added in an amount effective to achieve natural buoyancy of the microcapsule. Examples of such dense lipids include, but are not limited to, triethyl citrate, tributyl citrate, and triacetin.

The pest-control microcapsule of the present invention can also include an antioxidant in the diluent. Addition of an antioxidation agent enhances the oxidative stability of the diluent and, therefore, prolongs potency of the microcapsule as well. Examples of such antioxidation agent include vitamin E oil and synthetic food-grade antioxidants. Sun screen (such as carbon black or other UV absorbers) can also be added in order to provide protection from sun light.

The microcapsules of the present invention can be formed by processes, such as complex coacervation, solvent evaporation, interfacial polymerization (IFP), or in-situ polymerization encapsulation protocols. With IFP protocols, multifunctional acid chloride and isocyanate are employed as shell-forming agents. When the active pest-control agent contains a functionality readily reacting with acid chloride or isocyanate, microcapsules can be formed by complex coacervation, in situ polymerization or solvent evaporation.

In another aspect, this invention features a method of long-term pest control. The steps of the method include mixing an active pest-control agent with an inactive, biodegradable, and nontoxic diluent to the extent effective to entrap the active ingredient by the diluent; microencapsulating the mixture to form a microcapsule with a capsule core and shell; providing resistant mass transfer paths for the active ingredient in the capsule core and the shell; and sustaining the rate of release of the active ingredient through the core and the shell. In particular, the new method can accomplish better entrapping of the active ingredient by dissolving the active ingredient in the diluent in liquid state, and entrapping the active ingredient by the diluent, in which solid diluent is melted at a temperature below 80°–90°.

The method also allows the formulator to select a release rate of the active ingredient suitable for pest control and the characteristics of the surrounding medium. For example, the release rate of the active ingredient through the capsule core can be adjusted by manipulating the amount or percentage of the diluent, distribution pattern of the diluent, method of entrapping the active ingredient in the diluent, physical properties of the diluent including its melting point, and temperature of the surrounding medium. Furthermore, the release rate of the active ingredient through the shell can be adjusted by manipulating the composition and homogeneity of the capsule shell, thereby affecting the size, length, density, tortuosity, distribution, and properties of any pores in the shell and diffusivity of the active ingredient through the shell free of pores.

Ease of use or utility of the pest-control microcapsules prepared by any of the above methods can be improved by adding to the diluent a water-immiscible compound heavier than water and having at least one ester linkage in an amount effective to increase resulting density of said microcapsules very close to 1.0. For example, the water-immiscible compound can be added in an amount effective to make resulting microcapsules sink slowly in an aqueous solution or achieve natural buoyancy. Dense microcapsules prepared by these new methods will not float in an aqueous solution and will not form a creamed layer on storage which has detrimental effects on ease of preparing the capsule suspension for field applications.

The potency as well as the shelf life of the pest-control microcapsules prepared by the above methods can also be improved by adding an antioxidation agent to the diluent and/or by adding a sun screen such as carbon black or other UV absorbers.

As used herein, "core material", of a microcapsule is the material in a microcapsule containing an active pest-control agent to be carried by the microcapsule and to provide effective pest control.

A "microcapsule shell" is, as used herein, the coating, membrane and/or wall that surrounds the volume material of the microcapsule in which the active ingredient is located. The microcapsule shell provides a physical barrier that separates the contents of the microcapsule from the exterior or surrounding medium in which microcapsules are immersed or placed.

A "pest-control agent" is any compound that is toxic to an insect at any stage of its development when ingested or brought into contact with the target insects in some manner (e.g., pyrethroids), any agent that disrupts mating of the target insects (pheromones), any agent that alters the growth and development of insects at some stage of their development (e.g., insect growth regulators), or any agent that acts as an attractant to a "trap" at which the insect is terminated in some manner (e.g., by electric shock, drowning, or physical entrapment as on a sticky surface).

As used herein, a biopesticide is any active pest-control agent that is nontoxic to mammalians. Examples of biopesticides include, but are not limited to, pheromones, pyrethroids, and insect growth regulators.

As used herein, "diluent" means a liquid or solid with a low melting point, for example, 80° C.–90° C., in which the active pest-control agent is soluble either at room temperature or below, at the temperature at which microcapsule formation is carried out (typically at 40°–60° C.), or at the melting temperature of the diluent. Diluents may consist of a single chemical compound or may be a mixture of several components where such diluents are natural products which in their conventional form are composed of multiple components.

As used herein, toxicity generally pertains mainly to mammalians, therefore, plants and fruits treated by the nontoxic pest-control microcapsules are edible.

Unless otherwise defined, all technical and scientific terms used herein have the same meaning as commonly understood by one of ordinary skill in the art related to this invention. Other methods and materials in addition to those specifically described herein can be used in the practice of the present invention. All publications, patent applications, patents, and other references mentioned herein are incorporated by reference in their entirety. In case of conflict, the present specification, including definitions, will control. The materials, methods, and examples are illustrative only and not intended to be limiting.

Other features and advantages of the invention will be apparent from the following detailed description, and from the claims.

The invention features a sustained-release, long-term pest-control microcapsule which is environmentally friendly and non-toxic, and prolongs its potency by controlling the nature of the diluent in the capsule core in which the pest-control agent is dissolved or dispersed.

In general, a microcapsule includes a capsule core and a capsule shell, both of which can provide resistant paths to the mass transfer of the active pest-control agent contained in the capsule core. Thus, the pest-control microcapsule of the present invention is designed to reduce the rate of release of active ingredient distributed into the surrounding medium, thereby reducing the cost of pest control as well as the potential for environmental pollution by utilizing interactions between the active ingredient and the diluent either in the solid or liquid state.

Diluents used in the microcapsule are selected from the class of materials defined as lipids. Some may form liquid at room temperature and below, while others form solids with low melting point, for example, lower than 80° C.–90° C. Most lipid diluents include one or more ester linkages where one component of the ester linkage is a fatty acid which is classified as either a short-, medium- or long-chained fatty acid. However, other components without any ester linkage, for example, cholesterol, can also be used as a lipid diluent.

Diluent lipids are often isolated from natural sources (e.g., various plant and animal oils or waxes), are biodegradable, and are non-toxic to all forms of life, thus, generally edible. Examples of diluent lipids include, but are not limited to, plant oils of commerce such as corn oil, soybean oil, canola oil, peanut oil, olive oil, palm oil, coconut oil, cottonseed oil, and sunflower oil. Mixtures of these oils as well as refined or purified oils obtained therefrom can also be used. Such oils refined for specific food or pharmaceutical applications may be classified as oils rich in short-, medium- or long-chained fatty acids. Fats with low melting point produced by varying the degree of hydrogenation of the aforementioned oils or isolated by selective crystallization from various plant oils can also be used. Oils derived from an animal source such as butterfat oil, and low melting point fats from animals such as butterfat and lard can be used as well, although some animal oils may require additional stability control. Natural waxes like bee wax (actually an insect wax produced by bees), carnauba wax (a plant wax), candellila wax (a plant wax), and paraffin wax can also be used. Mixture of these various oils, hydrogenated oils, and waxes derived from various plant or animal source can also be used. A purpose of mixing various oils and waxes is to alter the crystallization temperature of the waxes or hydrogenated oils, thereby altering the temperature at which they soften.

Various aforementioned lipids are relatively pure compounds which may either be isolated from the above mentioned natural plant oil and wax sources or can be prepared by completely synthetic means. Examples include triglycerides such as tristearin, tripalmitin, and trilaurin, as well as triglycerides containing a mixture of one or more different fatty acids. In addition, natural or formulated mixtures of triglycerides, diglycerides, and monoglycerides with or without the additional presence of various free fatty acids can also be used, for such mixtures in reality represent the actual composition of the various plant lipids and animal oils aforementioned.

The formulator can customize the melting point of the diluent by manipulating the size and chemical structure of the lipid. For example, the melting point of the lipid including oils, waxes, and fats can vary over a wide range of temperature by manipulating the number of ester linkages as well as the number and characteristics of the short-, medium-, and long-chained fatty acids attached to those ester linkages.

The diluent is distributed in the core in such a manner that the active pest-control agent is dispersed or dissolved in the diluent and must diffuse through the resistant paths formed by the diluent to reach the capsule shell through which it must subsequently diffuse in order to be released from the capsules. The diluent may operate in several ways. One possible way is that the lipid and pest-control agent have a strong affinity for each other (i.e., mutually miscible) and this affinity reduces the tendency for the pest-control agent to diffuse through the shell. In this case, the AI-lipid mixture may form a liquid at room temperature. Alternatively, the diluent may form a solid-like, matrix-like or mesh-like structure inside the core which effectively entraps the active ingredient inside such matrix and mesh, thereby delaying release thereof. Thus, a formulator can obtain desirable permeability or release rate of the active ingredient by manipulating several factors, such as the amount or percentage of the diluent contained in the capsule core, distribution pattern of the diluent in the core, method of entrapping the active ingredient in the diluent, and other chemical and/or physical properties of the diluent.

The sustained-release, pest-control microcapsule of the present invention may be made of biodegradable and non-toxic compounds. The pest-control microcapsules can include in its core a bio-pesticide such as pheromones, pyrethroids, and insect growth regulators as well as an inactive, biodegradable and nontoxic lipid diluent such as oils, waxes, and fats with ester linkages or cholesterol. However, conventional toxic pest-control agents can also be used along with the inactive, biodegradable, and nontoxic lipid diluent.

Examples of active, biodegradable, and nontoxic pest-control agents include, but are not limited to, biopesticides such as pheromones, pyrethroids, insect growth regulators, and insect attractants or repellents. Conventional toxic pesticidal agents, however, can also be used in conjunction with the aforementioned inactive, bio-degradable, and non-toxic diluents.

The capsule shell separates the core volume material from the surrounding medium, and provides the additional resistant paths, for example, the shell pores and/or other paths, through which the active pest-control agent diffuses into the medium. Thus, permeability or release rate of the active ingredient can be manipulated by controlling at least one of the several factors such as the pore size, length, density, tortuosity, pattern of pore distribution in the shells, and other physical properties of the material constituting the shell. Details as to the formation of such capsule shells will be discussed in greater detail below.

The microcapsules of the present invention may be formed by any of the processes such as complex coacervation, solvent evaporation, interfacial polymerization (IFP), and in-situ polymerization. With IFP, multi-functional acid chloride and isocyanate are used as shell-forming agents. However, when the active pest-control agent contains a functionality which may readily react with acid chloride or isocyanate, microcapsules can be formed by the processes such as complex coacervation, in situ polymerization or solvent evaporation protocols.

Suitability of a given diluent/active pest-control agent for encapsulation can be defined by forming a series of mixtures of active pest-control agents with candidate diluents. When observed visually, they provide a means of assessing whether or not mixtures form a homogeneous solution, and are mutually miscible or compatible. For example, following Examples 1 and 2 summarize some exemplary observations of compatibility of selected diluents and active pest-control agents.

EXAMPLE 1

Compatibility Test Results

| MIXTURE | COMPATIBILITY |
| --- | --- |
| Beeswax (6 g) OFM* (6 ml) | Formed a homogeneous solution above 60° C.; formed a mushy, soft solid when cooled to 22° C. |
| Yellow Carnauba Wax (5 g) OFM (5 ml) | Formed a homogeneous solution above 70° C.; formed a very hard solid when cooled to 22° C. |
| Hydrogenated tallow (5 g) OFM (5 ml) | Formed a homogeneous solution above 40° C.; formed a soft but brittle solid when cooled to 22° C. |
| Candellila Wax (5 g) OFM (5 ml) | Formed a homogeneous solution above 60° C.; formed a very hard solid when cooled to 22° C. |
| Paraffin Wax (5 g) OFM (5 ml) | Formed a homogeneous solution above 42° C.; formed a hard solid when cooled to 22° C. |
| Dark chocolate (5 g) OFM (5 ml) | Formed liquid at 22° C.; solidified at 5° C. (i.e., in refrigerator) |

*Oriental fruit moth pheromone

EXAMPLE 2

Compatibility Test Results Using Pheromone (CM)

| MIXTURE | COMPATIBILITY |
| --- | --- |
| Beeswax (5 g) CM (5 ml) | Homogeneous solution above 55° C.; Solid at room temperature (22° C.) |
| Yellow Carnauba Wax (5 g) CM (5 ml) | Homogeneous solution above 73° C.; Solid at 22° C. |
| Hydrogenated Tallow (5 g) CM (5 ml) | Homogeneous solution above 41° C.; Solid at 22° C. |
| Dark chocolate (5 g) CM (5 ml) | Liquid at 22° C. Homogeneous solution |
| Candellila Wax (5 g) CM (5 ml) | Homogeneous solution above 60° C.; Solid at 22° C. |

EXAMPLE 3

Evaluation Method Protocol

Miscibility of the active ingredient and diluents were further examined by forming mixtures of various active ingredients (pheromones) with corn oil or triethylcitrate. The final composition of the mixture produced was 40 vol. % pheromones and 60 vol. % diluent (i.e., corn oil or triethyl citrate). The individual pheromones evaluated were: tomato pinworm, pink bollworm, leafroller, oriental fruitmoth, and coddling moth. All of these pheromones were completely miscible at room temperature in corn oil or triethylcitrate (40 vol. % pheromones/60 vol. % diluent). It was notable that coddling moth pheromones formed solid at room temperature, but dissolved freely in both corn oil and triethyl citrate. In general, it was found that pheromones and pyrethroids were mutually miscible in the various diluents at a 40 vol. % active ingredient/60 vol. % diluent ratio.

EXAMPLE 4

Microencapsulation by Interfacial Polycondensation

Microcapsules were prepared using the core material which was a mutually miscible mixture of the active ingredient and the diluent. For example, pink bollworm pheromone was dissolved in a purified lipid oil (Miglyol 812) such that the mixture contained 40 vol. % pink bollworm pheromone and 60 vol. % Miglyol 812. To this mixture (137 ml) was added a multi-functional isocyanate (e.g., Mondur MRS) (27.4 ml). The resulting mixture was emulsified in a aqueous medium that contained a dispersing agent (e.g., partially hydrolyzed poly(vinyl alcohol—0.25 to 5 wt. %). Once the desired oil phase droplet size was obtained, a multi-functional amine (e.g., ethylene diamine, diethylene triamine, or triethylene tetramine) was added to the aqueous phase to thereby initiate formation of a capsule shell. The reaction responsible for formation of a polyurea capsule shell was allowed to proceed for a finite time period (e.g., 1–8 hours) at an elevated reaction temperature (e.g., 40°–60° C.). The microcapsules produced in this manner, when isolated and dried with a small amount of solid drying aid like fumed silica (e.g., Cab-O-Sil M-5), formed free-flowing powder which produced no visible stain when stored for a prolonged period on paper, evidencing that the microcapsules did not leach their nonvolatile diluent core at a finite rate. Furthermore, the microcapsule powder remained as free-flow powder when stored for prolonged periods in closed storage containers, further evidencing that the microcapsule shell formed had superior barrier properties.

The above microencapsulation protocol had been successfully repeated with leafroller, oriental fruit moth, and tomato pinworm with pheromones as the active ingredient. The amount and composition of the core material were held constant in these encapsulation runs as was the actual encapsulation protocol. The success of this series of experiments demonstrated the microcapsules with superior barrier properties.

All of the above-mentioned pheromones can be substituted in the same encapsulation protocol where shell formation occurs by interfacial polycondensation, because all of these agents are stable compounds free of reactive functional groups that are chemically reactive with compounds such as isocyanates and acid chlorides. Since these latter reactive compounds are dissolved in the core phase along with the pheromone selected to be encapsulated with the diluent, such reactive functionalities will likely react with any functional group located on the active pest-control agent. Because the aforementioned pheromones do not have a reactive functional group, there will not be any such reaction. However, with other active pest-control agents, chemically reactive functionalities are present that may inhibit the formation of microcapsule shells by interfacial condensation. An alternate encapsulation protocol may be used, and/or the extent of reaction between reactive acid chloride or isocyanate functionalities with reactive functionalities located on the active ingredient may be reduced to essentially zero to prevent formation of new molecular species with undefined biological activity and toxicity. Accordingly, microcapsule shells with such active ingredient may be formed by an encapsulation protocol other than interfacial polycondensation, for example, complex coacervation and in situ polymerization of urea and/or melamine with formaldehyde, as illustrated in the following example.

EXAMPLE 5

Microencapsulation of the Active ingredient with Reactive Functionality

Coddling moth pheromone contains a hydroxyl functionality that is potentially reactive with acid chloride or isocyanate functionalities. In situ polymerization was used to produce the microcapsule shells. No compounds with a reactive group were introduced into the core material in order to cause formation of the microcapsule shells. All reactive compounds responsible for capsule shell formation were located in the aqueous medium in which the core material was suspended or dispersed.

Coddling moth pheromone (35 mg) was dissolved in 59 ml Miglyol 812, the diluent. The mixture was emulsified in 100 ml of an aqueous solution of ethylene-maleic acid copolymer solution in which 7 g of urea and 0.4 g of ammonium chloride were dissolved. Once the desired size of desired oil phase droplets had been reached, formaldehyde was added (17.5 ml 37% solution), the system was heated to 40–60° C., and was allowed to react for 2–6 hours. The capsule produced in this manner, when isolated and dried with a small amount of solid drying aid like fumed silica (e.g., Cab-O-Sil M-5), formed a free-flowing powder which produced no visible stain when stored for a prolonged period on paper, evidencing that the microcapsules did not leach their non-volatile diluent core at a finite rate. Furthermore, the microcapsule powder remained as free-flow powder when stored for prolonged periods in closed storage containers, further evidencing that the microcapsule shell formed had superior barrier properties.

A pest-control microcapsule can be composed in such a way that the permeability or release rate of the active ingredient depends upon the melting point of the diluent and the temperature of the surrounding medium. Lipids such as oils, waxes, and fats with at least one ester linkage or cholesterol are used as diluents and incorporated into the capsule core through microencapsulation. In general, these lipids have melting points of 80°–90° C. or lower, or may gradually melt over a wide range of temperature when the diluents consist of a mixture of various lipids with different melting points. Thus, when the temperature of the surrounding medium rises near or above the melting point of the lipid, i.e., usually during the season and/or the time of the day with high insect activity or mating, the lipid diluent begins to soften or melt and the active ingredient previously entrapped by those lipid diluent is released and diffuses into the medium at a higher rate. However, when the temperature falls below the melting point of these lipids and enough to suppress insect activities, the lipid diluent hardens or solidifies, and effectively sustains the release of the active ingredient by re-entrapping the active pest-control agent in the hardening or solidifying lipid.

In addition, the lipid has a high boiling point, e.g., higher than 200° C. at atmospheric pressure with the possibility of accompanying decomposition and, therefore, hardly evaporates. Accordingly, the potency of the pest-control microcapsule can be effectively prolonged adaptive to the temperature of the surrounding medium. Example 6 illustrates the field test results of long-term potency of the microcapsules, which was also presented at the 73rd Annual Western Orchard Pest & Disease Management Conference, Imperial Hotel, Portland, Oreg., during Jan. 6–9, 1999. Relevant portions of the Proceedings, entitled, "Behavior of Microencapsulated Coddling Moth and Oriental Fruit Moth Pheromone Formulations In California Field Test," are incorporated herein by reference.

EXAMPLE 6

Field Test Results of Pheromone Formulations

Field studies were carried out in California to evaluate the behavior of two microencapsulated coddling moth (CM) and two microencapsulated oriental fruit moth (OFM) pheromone formulations. The OFM formulations (Formulations A and B) were applied at 20 gms. actives per acre to 10 acre blocks of almonds in Kern County, Calif., with a tractor drawn sprayer on Jul. 6, 1998. The CM formulations (Formulations C and D) were applied at 20 gms. actives per acre by helicopter to 10 acre blocks of Serr walnuts in Tulare County, Calif., on Jul. 24, 1998. Four lure baited winged sticky traps placed in each treated block were checked periodically for moth capture. Control traps (four for OFM-treated blocks and two for CM-treated blocks) were placed approximately one mile upwind from the treated blocks. Reported trap counts are mean values recorded at the time periods specified.

Table 1 contains trap count data for OFM-treated almond blocks. For the first 51 days post-spray, both formulations reduced the trap count to zero. At days 63 through 93 post-spray, trap counts in both treated blocks remained low. During the first 93 days post-spray, a total of four moths were caught in traps in the block treated with Formulation A while three moths were captured in the block treated with Formulation B during the same period. The trap count increased significantly at 98 days post-spray. Thus, a single application of the two OFM-loaded microcapsule formulations reduced moth capture in the treated almond blocks to a very low level throughout this period. This is attributed to their ability to release OFM at a finite rate throughout the test.

TABLE 1

Mean number of oriental fruit moths captured at various times after application of microencapsulated OFM pheromone formulations as a spray on almond trees at a rate of 20 gm. actives/acre.

| | Mean number of moths captured | | | | | | | | | |
|---|---|---|---|---|---|---|---|---|---|---|
| Days after spraying | 7 | 18 | 28 | 38 | 51 | 60 | 72 | 81 | 93 | 98 |
| Microcapsule formulation A | 0 | 0 | 0 | 0 | 0 | 0.25 | 0 | 0.75 | 0 | 6.5 |
| Microcapsule formulation B | 0 | 0 | 0 | 0 | 0 | 0 | 0.25 | 0.25 | 0.25 | 2.5 |
| Control | 10 | 4.8 | 10.8 | 9.0 | 26.3 | 18.0 | 12.3 | 38.8 | 16.8 | 10.8 |

Table 2 contains trap count data for CM-treated Serr walnut blocks. Formulation C reduced the coddling moth trap count to zero for 18 days post-spray. The mean trap count increased to 1.25 moths at 32 days post-spray, but this still represented a 93.9% reduction in trap count relative to control. Formulation D gave zero trap count for 11 days post-spray, but the trap count at days 18, 32 and 47 post-spray was reduced by 95–97% relative to control. Both microencapsulated CM pheromone formulations at days 53 and 62 post-spray gave trap counts significantly higher than control. The reduction in trap count caused by the microencapsulated CM formulations is taken as evidence that the capsules released CM pheromone at a finite rate throughout the test.

TABLE 2

Mean number of coddling moths captured at various times after application of microencapsulated CM pheromone formulations as a spray on Serr walnut trees at a rate of 20 gm. actives/acre.

| | Mean number of moths captured | | | | | |
|---|---|---|---|---|---|---|
| Days after spraying | 11 | 18 | 32 | 47 | 53 | 62 |
| Microcapsule formulation C | 0 | 0 | 1.25 | 3.0 | 9.0 | 24.0 |
| Microcapsule formulation D | 0 | 0.25 | 0.75 | 0.5 | 12.75 | 27.25 |
| Control | 17.5 | 9.5 | 20.5 | 11.0 | 8.5 | 13.0 |

The data in Tables 1 and 2 indicate that the microcapsule formulations evaluated caused a significant reduction in the number of coddling or oriental fruit moths captured in traps over a prolonged period.

The observations reported here might be unique to the conditions that existed in California during the test. No rain fell on any of the test blocks throughout the test period. Furthermore, temperatures in the region of the test blocks were high throughout much of the test period. Daily high temperatures were primarily 35–40° C. and daily low temperatures were primarily 17–22° C. until day 72 post-spray of the OFM test and day 53 post-spray of the CM test. In spite of these elevated temperature conditions, the microencapsulated CM formulations remained highly effective in causing trap count reduction for periods of 32–47 days. This was significant, because CM pheromone was susceptible to degradation. Scanning electron micrographs of leaf surfaces showed that the CM capsules were in various stages of deterioration at approximately 42 days post-spray.

The results reported here provide encouragement that microencapsulated pheromone formulations capable of multi-month field life could be produced and microcapsules loaded with pheromones susceptible to degradation could remain active in the field for a multi-week period.

The pest-control microcapsule of the present invention may have a density comparable to that of water. Generally, lipid diluents are lighter than water arid, therefore, microcapsules containing sufficient amount of such lipids float in an aqueous solution on storage. The creamed layer formed by clogged microcapsules may adversely affect the potency and performance characteristics of the microcapsules. Accordingly, a water-immiscible compound, having at least one ester linkage and having a density greater than that of water, may be added to the lipid diluent in an amount effective to make the microcapsules sink slowly in an aqueous solution. Such water-immiscible compound can also be added in an amount effective to achieve natural buoyancy of the microcapsule. Examples of such dense lipids include triethyl citrate, tributyl citrate, and triacetin.

The pest-control microcapsule may also include one or more antioxidants in the diluent as well as one or more sunscreen agents which are known in the art to block the action of light in some manner, for example, carbon black or UV absorbers. Addition of antioxidants or sunscreens may enhance the oxidative stability of the diluent and, therefore, prolongs potency of the microcapsule as well. Examples of such antioxidation agent include vitamin E oil and synthetic food-grade antioxidants.

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

What is claimed is:

1. Sustained-release microcapsule for long-term pest control made by the process of:
dissolving an active pest-control ingredient comprising at least one pheromone with an inactive, biodegradable, and non-toxic lipid diluent to form a mixture;
entrapping said active ingredient inside said diluent;
microencapsulating said mixture in order to form a plurality of microcapsules consisting essentially of a capsule core and capsule shell; and
providing resistant paths for mass transfer of said active ingredient to at least one of said capsule core and said capsule shell,
wherein said mass transfer resistance depends on the temperature of the surrounding medium; and
wherein said microencapsulating further comprises:
manipulating at least one of amount of said diluent, percentage of said diluent, distribution pattern of said diluent, method of entrapping said active ingredient by said diluent, physical properties of said diluent comprising melting point thereof, and temperature of the surrounding medium, to thereby vary said mass transfer resistance to said active ingredient through said capsule core; and/or manipulating at least one of pore size, pore length, pore density, pore tortuosity, pattern of pore distribution, physical properties of said capsule shell comprising melting point thereof, and temperature of the surrounding medium, to thereby vary said mass transfer resistance to said active ingredient through said capsule shell.

2. A method of long-term pest control comprising the steps of:

dissolving an active ingredient comprising at least one pheromone with an inactive, biodegradable, and non-toxic lipid diluent to form a mixture;

entrapping said active ingredient by said diluent;

microencapsulating said mixture in order to form a plurality of microcapsules consisting essentially of a capsule core and capsule shell;

providing resistant paths for mass transfer of said active ingredient in said capsule core and through said capsule shell; and sustaining the rate of release of said ingredient through said capsule core and said capsule shell depending on the temperature of the surrounding medium;

wherein said microencapsulating further comprises:

manipulating at least one of amount of said diluent, percentage of said diluent, distribution pattern of said diluent, method of entrapping said active ingredient by said diluent, physical properties of said diluent comprising melting point thereof, and temperature of the surrounding medium, to thereby vary said mass transfer resistance to said active ingredient through said capsule core; and/or manipulating at least one of pore size, pore length, pore density, pore tortuosity, pattern of pore distribution, physical properties of said capsule shell comprising melting point thereof, and temperature of the surrounding medium, to thereby vary said mass transfer resistance to said active ingredient through said capsule shell.

3. Pest-control method according to claim 2, wherein said dissolving step further comprises:

melting said diluent at a temperature below 90° C.;

dissolving said active ingredient; and providing said mixture of said active ingredient and said diluent.

4. Pest-control method according to claim 2, further comprising the steps of:

adding a water-immiscible lipid to said diluent, said water-immiscible lipid being heavier than water and having at least one ester linkage in an amount effective to increase the resulting density of said microcapsules very close to 1.0;

forming said microcapsule; and preventing said microcapsule from floating and forming a creamed layer on storage in an aqueous solution thereof.

5. Pest-control method according to claim 4, wherein the step of adding said lipid further comprises:

adding said water-immiscible lipid to said diluent in an amount effective to make said microcapsule sink slowly in said solution.

6. A method of long-term pest control comprising the steps of:

dissolving an active ingredient comprising at least one pheromone with an inactive, biodegradable, and non-toxic lipid diluent to form a mixture;

microencapsulating said mixture in order to form a plurality of microcapsules consisting essentially of a capsule core and capsule shell including resistant paths for mass transfer of said active ingredient; and sustaining the rate of release of said ingredient depending on the temperature of the surrounding medium;

wherein said microencapsulating further comprises:

manipulating at least one of amount of said diluent, percentage of said diluent, distribution pattern of said diluent, method of entrapping said active ingredient by said diluent, physical properties of said diluent comprising melting point thereof, and temperature of the surrounding medium, to thereby vary said mass transfer resistance to said active ingredient through said capsule core; and/or manipulating at least one of pore size, pore length, pore density, pore tortuosity, pattern of pore distribution, physical properties of said capsule shell comprising melting point thereof, and temperature of the surrounding medium, to thereby vary said mass transfer resistance to said active ingredient through said capsule shell.

* * * * *